(12) United States Patent
Osaki et al.

(10) Patent No.: US 10,441,229 B2
(45) Date of Patent: Oct. 15, 2019

(54) X-RAY CT APPARATUS

(71) Applicant: TOSHIBA MEDICAL SYSTEMS CORPORATION, Otawara-Shi (JP)

(72) Inventors: Hiroki Osaki, Nasushiobara (JP); Takahito Watanabe, Nasushiobara (JP); Shigeru Usuda, Otawara (JP)

(73) Assignee: Canon Medical Systems Corporation, Otawara-shi (JP)

( * ) Notice: Subject to any disclaimer, the term of this patent is extended or adjusted under 35 U.S.C. 154(b) by 223 days.

(21) Appl. No.: 15/694,214

(22) Filed: Sep. 1, 2017

(65) Prior Publication Data
US 2018/0070894 A1 Mar. 15, 2018

(30) Foreign Application Priority Data

Sep. 1, 2016 (JP) .................. 2016-170778

(51) Int. Cl.
- *A61B 6/04* (2006.01)
- *A61B 6/03* (2006.01)
- *A61B 6/00* (2006.01)

(52) U.S. Cl.
CPC ............ *A61B 6/0457* (2013.01); *A61B 6/032* (2013.01); *A61B 6/4447* (2013.01); *A61B 6/488* (2013.01); *A61B 6/54* (2013.01); *A61B 6/545* (2013.01); *A61B 6/0407* (2013.01)

(58) Field of Classification Search
CPC ..... A61B 6/032; A61B 6/0407; A61B 6/0457; A61B 6/4447; A61B 6/488; A61B 6/54; A61B 6/545
See application file for complete search history.

(56) References Cited

U.S. PATENT DOCUMENTS

| | | | |
|---|---|---|---|
| 2009/0147909 A1* | 6/2009 | Yoda | A61B 6/032 378/4 |
| 2009/0226066 A1* | 9/2009 | Williams | A61B 6/037 382/131 |
| 2014/0364718 A1 | 12/2014 | Teshigawara | |
| 2015/0279111 A1* | 10/2015 | Sugiura | G06T 7/0012 345/424 |

(Continued)

FOREIGN PATENT DOCUMENTS

| | | |
|---|---|---|
| JP | 10-14911 | 1/1998 |
| JP | 2013-236965 | 11/2013 |

(Continued)

*Primary Examiner* — Mark R Gaworecki
(74) *Attorney, Agent, or Firm* — Oblon, McClelland, Maier & Neustadt, L.L.P.

(57) ABSTRACT

According to one embodiment, an X-ray CT apparatus includes a gantry, a table on which an object is placed, a bed, and processing circuitry. The gantry is equipped with an X-ray source and an X-ray detector. The bed includes a moving mechanism which is configured to move the table in a horizontal direction and in a vertical direction. The processing circuitry performs a main scan and a prescan. The prescan is performed prior to the main scan. The processing circuitry calculates displacement of the table in the vertical direction and also calculates an angle of the table from the horizontal direction using data acquired in the prescan, and controls a position of the table and an angle of the gantry based on the displacement of the table and the angle of the table.

6 Claims, 11 Drawing Sheets

(56) References Cited

U.S. PATENT DOCUMENTS

| | | | |
|---|---|---|---|
| 2016/0117826 A1* | 4/2016 | Yan | G01B 11/26 348/135 |
| 2016/0143607 A1* | 5/2016 | Cao | A61B 6/5276 382/131 |
| 2016/0151024 A1* | 6/2016 | Goto | A61B 6/027 378/8 |
| 2017/0291042 A1* | 10/2017 | Takahashi | A61B 6/032 |

FOREIGN PATENT DOCUMENTS

| | | |
|---|---|---|
| JP | 2014-100553 | 6/2014 |
| JP | 2015-58227 | 3/2015 |

\* cited by examiner

X-RAY CT APPARATUS

CROSS-REFERENCE TO RELATED APPLICATIONS

This application claims the benefit of priority of Japanese Patent Application No. 2016-170778, filed on Sep. 1, 2016, the entire contents of which are incorporated herein by reference.

FIELD

Embodiments described herein relate generally to an X-ray CT apparatus.

BACKGROUND

A conventional X-ray CT (Computed Tomography) apparatus is an apparatus which images inside of an object (e.g. patient) by performing an X-ray scan on the patient and processing the acquired data with a computer. Specifically, an X-ray CT apparatus irradiates a patient with X-rays plural times from different directions along a circular orbit around the patient, and detects X-rays transmitted through the patient with an X-ray detector so as to acquire plural detection data. The acquired detection data are subjected to A/D (Analog to Digital) conversion and then transmitted to a console device.

In addition, an X-ray CT apparatus includes a bed equipped with a table on which an object is placed, and imaging of the object is generally performed in an X-ray CT gantry (X-ray scanner) of the X-ray CT apparatus. Further, the bed moves the table into a tunnel part inside the X-ray CT gantry such that the table is inserted in the longitudinal direction of the table. This movement is also referred to as a slide operation.

Since a table of an X-ray CT apparatus generally has such a structure that only one side of the table is supported, deflection occurs on the table due to weight of a patient thereon in the case of sliding the table during imaging. As a result, displacement and/or inclination is included in the acquired image in some cases. As to this problem, a method of correcting a reconstructed image with software has been studied.

However, in correction of such an image with the use of software, correction for smoothing the displacement is performed, but correction of inclination is not considered. In addition to this point, since correction by using hardware has not been implemented in conventional technology, there is a possibility that a patient is misdiagnosed on the basis of the acquired image subjected only to correction of smoothing displacement using software.

BRIEF DESCRIPTION OF THE DRAWINGS

The accompanying drawings, which are incorporated in and constitute a part of the specification, illustrate embodiments of the invention, and together with the general description given above and the detailed description of the embodiments given below, serve to explain the principles of the invention.

DETAILED DESCRIPTION

Hereinbelow, a description will be given of an X-ray CT apparatus according to embodiments of the present invention with reference to the drawings.

In general, according to one embodiment, an X-ray CT apparatus includes a gantry, a table on which an object is placed, a bed, and processing circuitry. The gantry is equipped with an X-ray source and an X-ray detector. The bed includes a moving mechanism which is configured to move the table in a horizontal direction and in a vertical direction. The processing circuitry performs a main scan and a prescan. The prescan is performed prior to the main scan. The processing circuitry calculates displacement of the table in the vertical direction and also calculates an angle of the table from the horizontal direction using data acquired in the prescan, and controls a position of the table and an angle of the gantry based on the displacement of the table and the angle of the table.

The X-ray CT apparatus as the medical image diagnostic apparatus 10 according to the embodiment may be of various types such as: a ROTATE/ROTATE type in which an X-ray tube and an X-ray detector integrally rotate around an object; and a STATIONARY/ROTATE type in which a large number of detecting elements are arrayed in a ring-like shape and only an X-ray tube rotates around an object. The present invention can be applied to any of the types. The following description, the ROTATE/ROTATE type is discussed.

Figure 1:
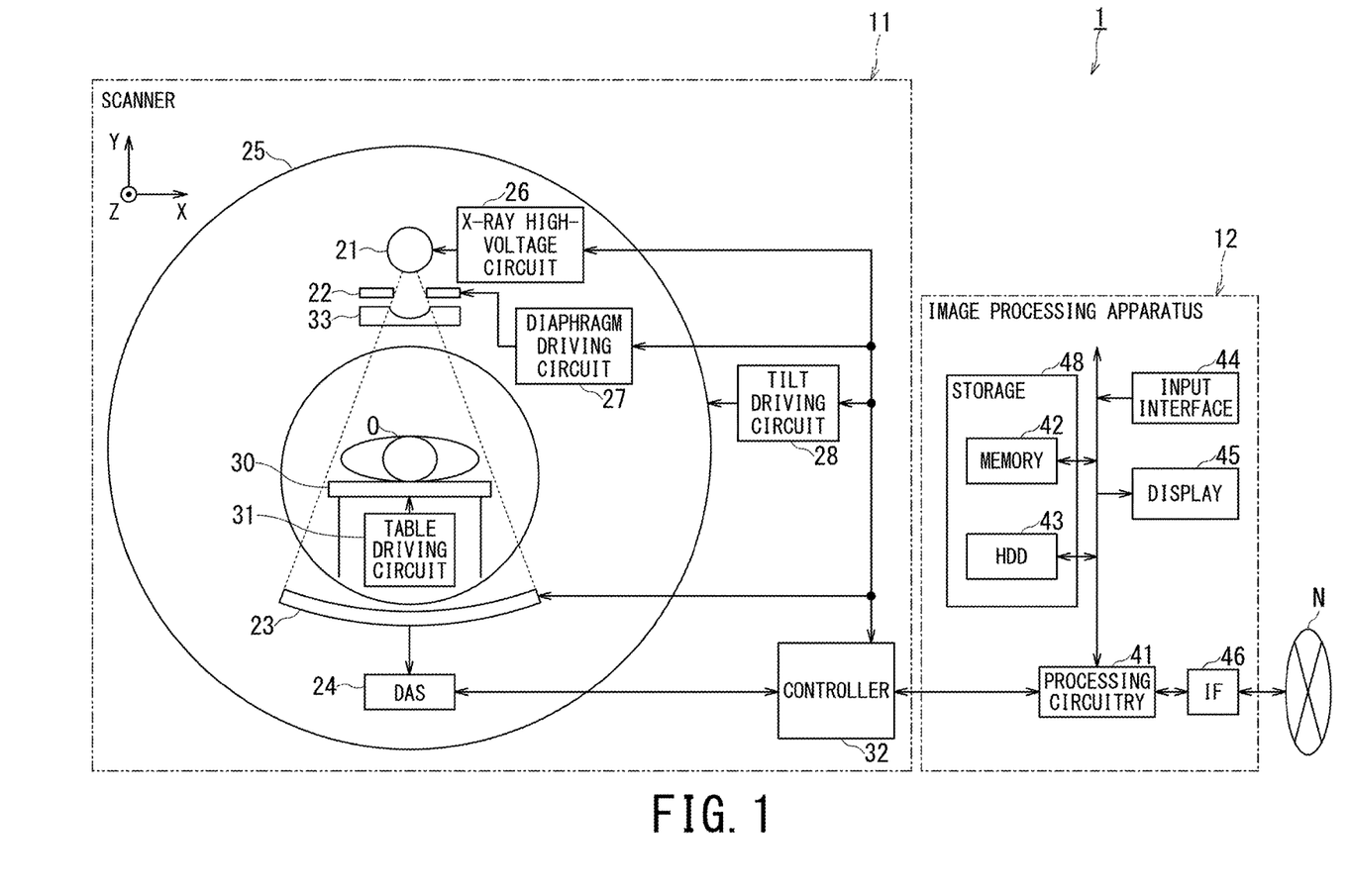
FIG. 1 is a diagram illustrating configuration of the X-ray CT apparatus according to the present embodiment.

FIG. 1 is a diagram illustrating configuration of the X-ray CT apparatus 1 according to the present embodiment.

The X-ray CT apparatus 1 is configured of a scanner 11 and an image processing apparatus 12. The scanner 11 of the X-ray CT apparatus 1 is usually installed in an examination room and is configured to generate X-ray transmission data on an object P. The image processing apparatus 12 is usually installed in a control room which is adjacent to the examination room, and is configured to generate and display reconstructed images by generating projection data on the basis of transmission data.

The scanner 11 of the X-ray CT apparatus 1 includes an X-ray tube 21, a diaphragm (collimator) 22, an X-ray detector 23, a DAS (Data Acquisition System) 24, a rotating body 25, an X-ray high-voltage circuit 26, a diaphragm driving circuit 27, a tilt driving circuit 28, a table 30, a table driving circuit 31, a controller 32, and a wedge (X-ray beam filter) 33. The X-ray tube 21 is one example of an X-ray source.

The X-ray tube 21 generates X-rays by bombarding a metal target with an electron beam according to the tube voltage supplied from the X-ray high-voltage circuit 26, and radiates the X-rays toward the X-ray detector 23. The X-rays emitted from the X-ray tube 21 form fan-beam X-rays or cone beam X-rays. Electric power required for X-ray irradiation is supplied to the X-ray tube 21 under the control of the controller 32 via the X-ray high-voltage circuit 26.

An X-ray source of the X-ray CT apparatus 1 is not limited to the X-ray tube 21. For instance, when the X-ray CT apparatus 1 is configured as a so-called fifth-generation CT apparatus, the scanner 11 may include the following three components as an X-ray source instead of the X-ray tube 21: a focus coil configured to focus an electron beam generated from an electron gun; a deflection coil configured to electromagnetically deflect the electron beam; and a target ring configured to generate X-rays by colliding with an electron beam which is deflected by passing through the half circumference of the object P.

The diaphragm 22 adjusts an irradiation range (irradiation field) of X-rays radiated from the X-ray tube 21 by the diaphragm driving circuit 27. In other words, an X-ray irradiation range at a fan angle or a cone angle can be changed by adjusting the opening of the diaphragm 22 by the diaphragm driving circuit 27.

The wedge 33 reduces a low-energy X-ray component before X-rays radiated from the X-ray tube 21 pass through the object P. In the wedge 33, width of its concave portion in the X direction is adjusted by a non-illustrated wedge driving device depending on an opening degree of the diaphragm 22. In accordance with the opening degree of the diaphragm 22, the wedge 53 is selected from, e.g., plural wedges having several types of concave portions.

The X-ray detector 23 is a one-dimensional array type detector equipped with plural detection elements in the channel direction and a single detection element in the column (slice) direction. Alternatively, the X-ray detector 23 is a two-dimensional array type detector equipped with plural detection elements arrayed in a matrix (i.e., arrayed in plural rows in the channel direction and in plural columns in the slice direction), and is also referred to as a multi-slice type detector. When the X-ray detector 23 is a multi-slice type detector, it is possible to acquire data of a three-dimensional region having width in the slice direction by scanning (CT imaging and CT fluoroscopy) during one rotation (volume scanning). The X-ray detector 23 detects X-rays radiated from the X-ray tube 21.

The DAS 24 amplifies signals of transmission data detected by respective detection elements of the X-ray detector 23, converts the signals into digital signals, and generates detection data. The detection data generated by the DAS 24 are supplied to the image processing apparatus 12 via the controller 32 of the scanner 11. In the case of performing CTF (Computed Tomography Fluoroscopy), the DAS 24 shortens an acquisition rate of detection data.

The rotating body 25 integrally supports the X-ray tube 21, the diaphragm 22, the X-ray detector 23, the DAS 24, the X-ray high-voltage circuit 26, and the diaphragm driving circuit 27. The rotating body 25 is configured to be able to rotate about the object P such that the X-ray tube 21, the diaphragm 22, the X-ray detector 23, the DAS 24, the X-ray high-voltage circuit 26, and the diaphragm driving circuit 27 included therein integrally rotate under the state where the X-ray tube 21 and the X-ray detector 23 face each other. The X-ray high-voltage circuit 26 may be supported by the rotating body 25. The direction parallel to the rotational center axis of the rotating body 25 is defined as a Z direction, and the plane orthogonal to the Z direction is defined by an X direction and a Y direction.

The X-ray high-voltage circuit 26 supplies power required for X-ray irradiation to the X-ray tube 21 under the control of the controller 32.

The diaphragm driving circuit 27 has a mechanism for adjusting an irradiation range at a fan angle or cone angle of X-rays in the diaphragm 22 under the control of the controller 32.

The tilt driving circuit 28 has a mechanism for rotating the rotating body 25 such that the rotating body 25 rotates about the cavity (tunnel portion) under the control of the controller 32 while maintaining its positional relationship. In addition, the tilt driving circuit 28 has a function of tilting a housing which houses the rotating body 25, with respect to the longitudinal direction of the table 30 under the control of the controller 32. The housing which houses the rotating body 25 in the scanner 11 is referred to as a gantry 11a.

The table 30 is configured such that the object P can be placed on the table 30. The table 30 is provided on a bed 31a to be described below.

The table driving circuit 31 has a mechanism for moving upward and downward the table 30 along the Y direction and entering/returning the table 30 into/from the gantry along the Z direction under the control of the controller 32. An opening is formed at the central portion of the rotating body 25, and the object P placed on the table 30 is inserted into the opening (i.e., cavity or tunnel portion).

The controller 32 includes components such as a memory and a CPU (Central Processing Unit) as a non-illustrated control circuit. The controller 32 controls the X-ray detector 23, the DAS 24, the X-ray high-voltage circuit 26, the diaphragm driving circuit 27, the tilt driving circuit 28, the table driving circuit 31, and the non-illustrated wedge driving device according to an instruction from the image processing apparatus 12 so as to cause these components to perform a scan.

The image processing apparatus 12 of the X-ray CT apparatus 1 is configured on the basis of a computer and can intercommunicate with a network (Local Area Network) N. The image processing apparatus 12 is configured of basic hardware such as processing circuitry 41 as control circuitry, a memory 42, a HDD (Hard Disc Drive) 43, an input interface 44, a display 45, and an network interface (IF) 46.

The processing circuitry 41 is interconnected to respective hardware components constituting the image processing apparatus 12 via a bus as a common signal transmission path. The image processing apparatus 12 may include a recording medium drive in some cases. Further, the memory 42 and the HDD 43 constitute storage 48.

The processing circuitry 41 executes programs stored in the memory 42 in response to a command inputted when, e.g., an operator such as a doctor operates the input interface 44 to input the command. Additionally or alternatively, the processing circuitry 41 loads programs stored in the HDD 43 and programs, which are transferred from the network N and are installed in the HDD 43, into the memory 42 so as to execute the loaded programs. Its details will be described below with reference to FIG. 3.

The memory 42 is a storage device including components such as a ROM (Read Only Memory) and a RAM (Random Access Memory). The memory 42 stores IPL (Initial Program Loading), a BIOS (Basic Input/Output System), and data, and is used for work memory of the processing circuitry 41 and/or temporary storage of data.

The HDD 43 is a storage device which stores data and programs installed in the image processing apparatus 12 (including OS (Operating System) and application programs). Further, it is possible to cause the OS to provide a GUI (Graphical User Interface) with which a basic operation can be performed with the input interface 44, by using many graphics to display information for an operator such as a surgeon on the display 45.

The input interface 44 is a circuit for inputting signals from an input device such as a pointing device (such as a mouse) and a keyboard which can be operated by an operator such as a doctor and/or an inspection engineer. The input device is assumed to be included in the input interface 44 in the present embodiment. In this case, an input signal in accordance with an operation is transmitted from the input interface 44 to the processing circuitry 41.

The display 45 is a display device having a function of displaying an image of an object. The display 45 includes a non-illustrated image composition circuit, a VRAM (Video Random Access Memory), and a screen. The image composition circuit generates composite data obtained by composing, e.g., character data of various parameters with image data. The VRAM develops composite data on the screen. The display 45 is configured of a display device such as a liquid crystal display and a CRT (Cathode Ray Tube), and displays acquired images.

The network IF 46 is configured of a connector which conforms to the parallel connection specification and the serial connection specification. The network IF 46 has a function of performing communication control in accordance with each standard and connecting with the network N through a telephone line, and thereby the network IF 46 connects the X-ray CT apparatus 1 to the network N.

The image processing apparatus 12 performs correction processing (preprocessing) such as logarithmic conversion and sensitivity correction on the detection data (raw data) inputted from the DAS 24 of the scanner 11 so as to generate projection data, and stores the projection data in a storage device such as the HDD 43. In addition, the image processing apparatus 12 performs processing of removing scattered radiation on the preprocessed projection data. The image processing apparatus 12 removes scattered radiation on the basis of values of projection data within an X-ray irradiation range. The image processing apparatus 12 performs scattered-radiation correction by subtracting the scattered radiation estimated from magnitude of values of the target projection data or the adjacent projection data from the target projection data. The image processing apparatus 12 generates (reconstructs) CT image data based on a scan by using the corrected projection data, stores the CT image data in a storage device such as the HDD 43, and causes the display to display the CT image data as a CT image (i.e., acquired image).

The image processing apparatus 12 can generate volume data by interpolating plural reconstructed CT image data. For volume data reconstruction, it is possible to use an arbitrary method such as a cone beam reconstruction method, a multi-slice reconstruction method, and an enlargement reconstruction method. By performing a volume scan with the use of a multi-slice type detector as the X-ray detector 23 in the above-described manner, the image processing apparatus 12 can reconstruct a wide range of volume data.

Figure 2:
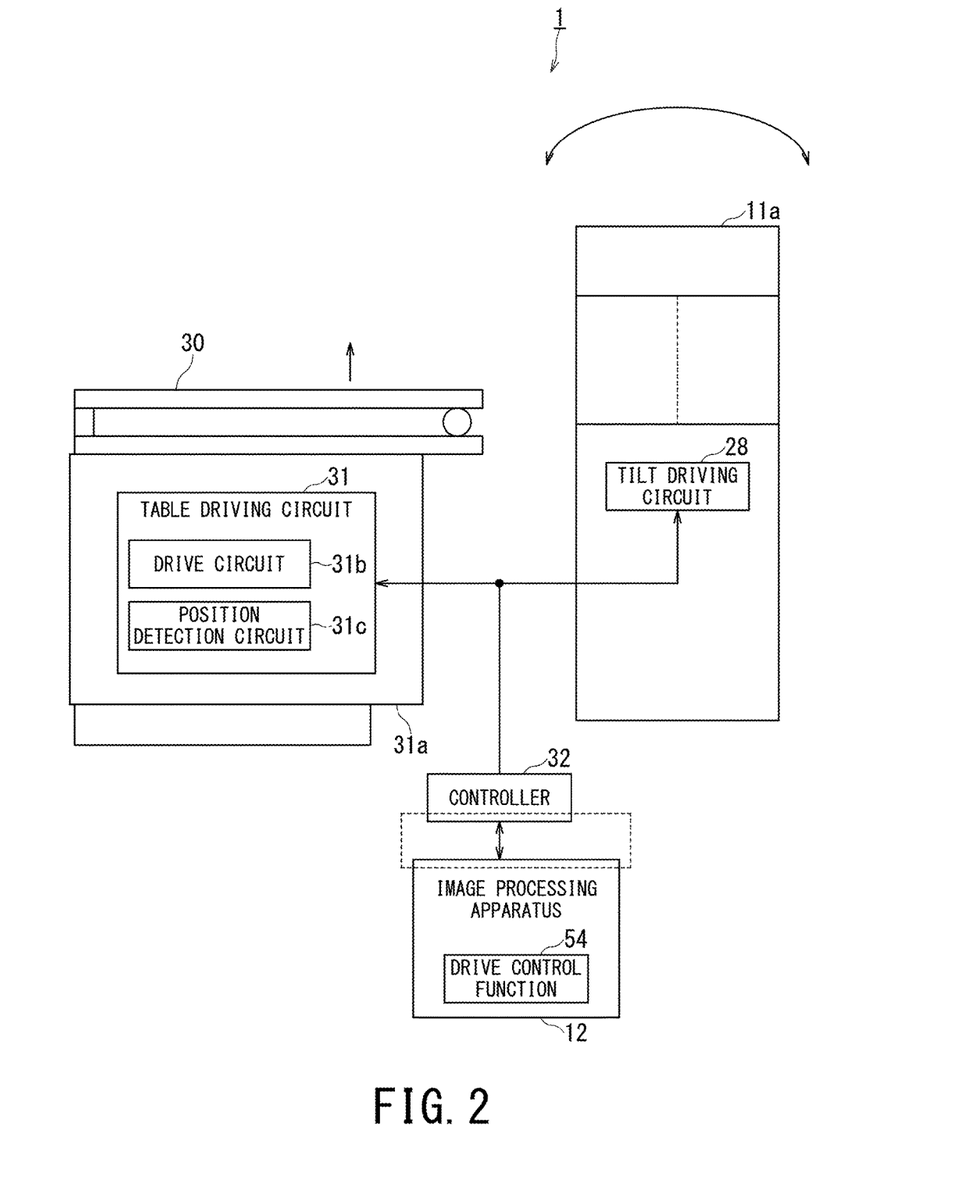
FIG. 2 is a configuration diagram illustrating hardware components relevant to correction in the X-ray CT apparatus according to the present embodiment.

FIG. 2 is a configuration diagram illustrating hardware components relevant to correction in the X-ray CT apparatus 1 according to the present embodiment.

As shown in FIG. 2, the X-ray CT apparatus 1 includes the bed 31a, the gantry 11a, and the image processing apparatus 12 as descried above.

The bed 31a includes the table 30 for placing the object P and the table drive circuit 31 as a moving mechanism for inserting the table 30 into the opening of the gantry 11a.

The table driving circuit 31 includes a drive circuit 31b for driving the table 30 and a position detection circuit 31c for detecting a position of the table 30. As described above, the table driving circuit 31 inserts the table 30 into the opening of the gantry 11a and returns the table 30 from the opening of the gantry 11a. Further, the table driving circuit 31 moves the table 30 upward and downward (i.e., in the vertical direction).

The drive circuit 31b may include a motor, and rotation number, a rotation direction, rotation speed, and the like of the motor are controlled by a drive control function 54 of the image processing apparatus 12 via the controller 32.

The position detection circuit 31c may include an encoder. The position detection circuit 31c detects rotation number, a rotation direction, rotation speed, and the like of the motor of the drive circuit 31b, and outputs them to the drive control function 54 of the image processing apparatus 12 via the controller 32.

The tilt driving circuit 28 tilts the gantry 11a in the longitudinal direction of the table 30 under the control of the controller 32.

The drive control function 54 controls the position of the table 30 in the vertical direction and the tilt angle of the gantry 11a at the time of a main scan via the controller 32 in order to correct the vertical displacement of the table 30 and the deviation angle of the table 30 from the horizontal direction, both of which are caused by deflection of the table 30. The drive control function 54 controls the drive circuit 31b and the tilt driving circuit 28 on the basis of positional information of the table 30 in the horizontal direction outputted from the position detection circuit 31c so as to control the position of the table 30 in the vertical direction and the tilt angle of the gantry 11a. This control will be described below with reference to FIG. 10 and FIG. 11.

Next, a description will be given of the function of the processing circuitry 41 of the image processing apparatus 12 for controlling the tilt driving circuit 28 and the table driving circuit 31 via the controller 32 of the scanner 11.

Figure 3:
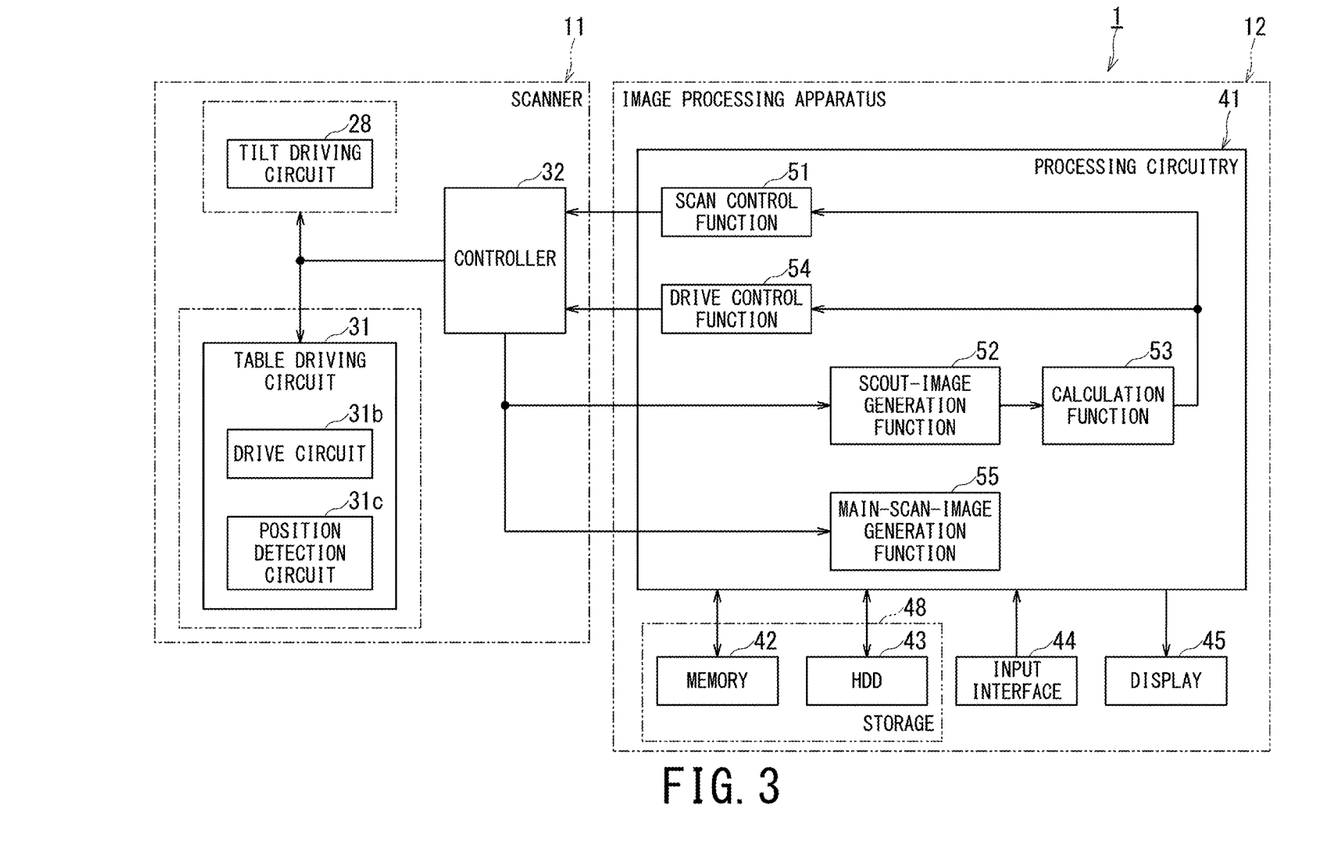
FIG. 3 is a block diagram illustrating the function of the processing circuitry in the image processing apparatus according to the present embodiment.

FIG. 3 is a block diagram illustrating the function of the processing circuitry 41 in the image processing apparatus 12 according to the present embodiment.

The processing circuitry 41 is a processor which implements functions corresponding to programs by reading out the programs from the memory 42 (storage 48) and executing the programs. Specifically, the processing circuitry (processor) 41 implements a scan control function 51, a scout-image generation function 52, a calculation function 53, the drive control function 54, and a main-scan-image generation function 55 by executing programs being read out from the memory 42.

The processing circuitry in the above-described embodiments is an example of the processing circuitry described in the claims. In addition, the term "processor" used in the explanation in the above-described embodiments, for instance, refer to circuitry such as dedicated or general purpose CPUs (Central Processing Units), dedicated or general-purpose CPUs (Graphics Processing Units), or ASICs (Application Specific Integrated Circuits), programmable logic devices including SPLDs (Simple Programmable Logic Devices), CPLDs (Complex Programmable Logic Devices), and FPGAs (Field Programmable Gate Arrays), and the like. The processor implements various types of functions by reading out and executing programs stored in the memory.

In addition, instead of storing programs in the memory, the programs may be directly incorporated into the circuitry of the processor. In this case, the processor implements each function by reading out and executing each program incorporated in its own circuitry. Moreover, although in the above-described embodiments an example is shown in which the processing circuitry configured of a single processor implements every function, the processing circuitry may be configured by combining plural processors independent of each other so that each processor implements each function of the processing circuitry by executing corresponding program. When a plurality of processors are provided for the processing circuitry, the memory medium for storing programs may be individually provided for each processor, or one memory like storage 48 shown in FIG. 1 may collectively store programs corresponding to all the functions of the processors.

Although the respective functions 51 to 55 of the image processing apparatus 12 of the X-ray CT apparatus 1 are assumed to be implemented when the processing circuitry 41 executes the programs, the present embodiment is not limited to such an aspect. All or some of the respective functions 51 to 55 of the X-ray CT apparatus 1 may be provided as hardware in the X-ray CT apparatus 1.

The scan control function 51 of the processing circuitry 41 executes a main scan and a prescan. The prescan is performed before the main scan. The scan control function 51 controls the controller 32 of the scanner 11 to acquire raw data (i.e., detection data) for generating a scout image in the prescan. In this case, the scan control function 51 controls the controller 32 such that tube current and tube voltage are supplied from the X-ray high-voltage circuit 26 to the X-ray tube 21 and the object P is irradiated with X-rays. Incidentally, a prescan is sometimes called a scout scan (scan for positioning).

In addition, the scan control function 51 executes a prescan such that slice width of the raw data to be acquired has a predetermined slice width from which the angle of the table 30 can be calculated. For instance, when acquiring raw data, the scan control function 51 performs a prescan by consecutively imaging the object P while moving the table 30. In this case, for instance, the scan control function 51 performs simultaneous multi-slice imaging in which slice data within the predetermined slice width are simultaneously acquired by one imaging. In the prescan, data are acquired by repeating the simultaneous multi-slice imaging while the table 30 is being moved.

The scout-image generation function 52 performs correction processing such as logarithmic conversion and sensitivity correction on raw data inputted from the DAS 24 of the scanner 11 so as to generate projection data, and stores the generated projection data in the HDD 43. Further, the scout-image generation function 52 generates projection data of plural cross-sections orthogonal to the Z direction on the basis of the projection data inputted from the HDD 43, generates a scout image on the basis of the projection data of the plural cross-sections, and store them in the storage 48 such as the HDD 43. Incidentally, raw data are sometimes simply referred to as data.

The calculation function 53 calculates displacement of the table 30 in the vertical direction and the angle formed by the table 30 and the horizontal direction with respect to the horizontal position of the table 30 using data acquired by a prescan. The calculation function 53 calculates displacement of the table 30 and the inclination angle of the table 30 using, e.g., a scout image.

The drive control function 54 controls the position of the table 30 and the angle of the gantry 11a at the time of a main scan on the basis of displacement of the table 30 and the angle of the table 30 as described above.

The drive control function 54 cooperates with the scan control function 51. The drive control function 54 controls the position of the table 30 in the vertical direction and the tilt angle of the gantry 11a. Concurrently, the scan control function 51 performs the main scan. The scan control function 51 acquires raw data for each view by controlling the controller 32 of the scanner 11 under the state where the position of the table 30 and the angle of the gantry 11a are adjusted.

The main-scan-image generation function 55 performs correction processing such as logarithmic conversion and sensitivity correction on the raw data at the time of the main scan inputted from the DAS 24 of the scanner 11 so as to generate projection data, and stores the generated projection data in the HDD 43. Further, the main-scan-image generation function 55 generates projection data of plural cross-sections orthogonal to the Z direction on the basis of the projection data inputted from the HDD 43, generates images of the main scan on the basis of the projection data of the plural cross-sections, and stores them in the storage 48 such as the HDD 43.

Here, in order to clarify the conventional problem, a description will be given of inclination of the table 30 and displacement (step difference) of the table 30 caused by the deflection of the table 30.

Figure 4:
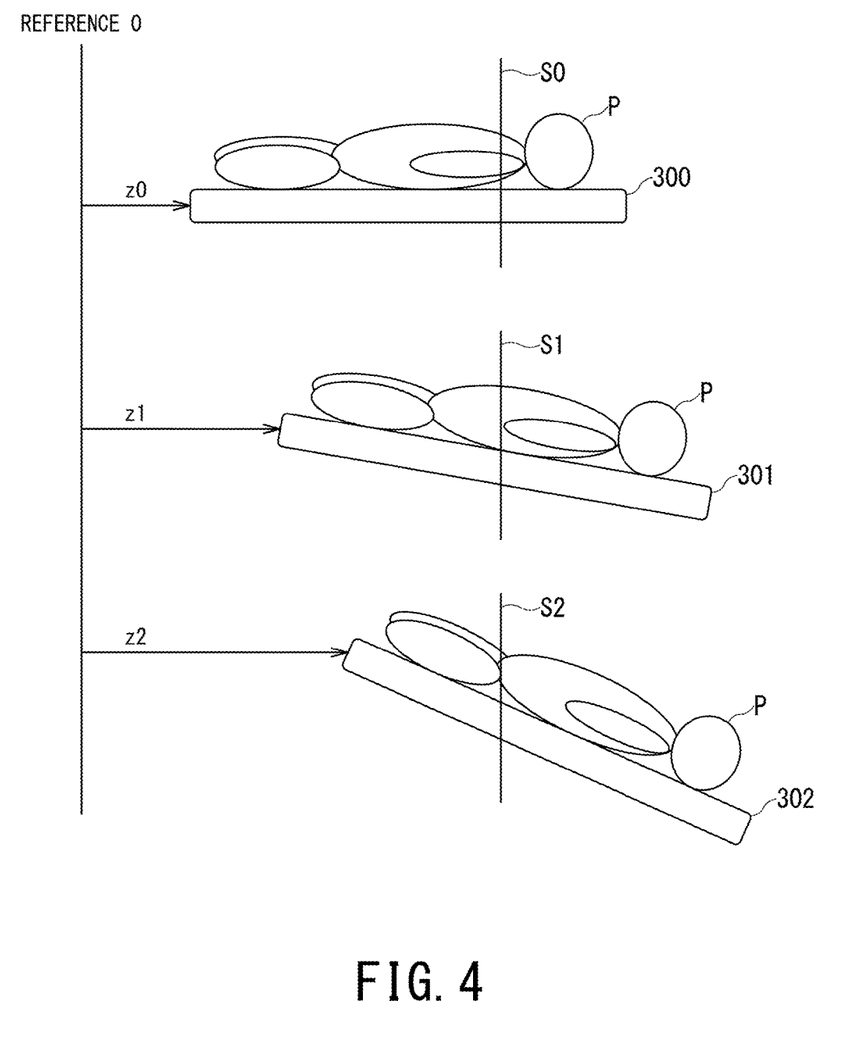
FIG. 4 is a schematic diagram illustrating change in the vertical position of the table and change in angle of the table, both of which are attributable to the respective sliding distances of the table from the bed to be determined by the imaging positions of the object, and is to discuss a conventional problem.

FIG. 4 is a schematic diagram illustrating change in the vertical position of the table 30 and change in angle of the table 30, both of which are attributable to the respective sliding distances of the table 30 from the bed 31a to be determined by the imaging positions S0, S1, S2 of the object P, and such change is a conventional problem. Actually, shape of the table 30 curves due to weight of the object F, but FIG. 4 focuses only on the change in the vertical position of the table 30 and change in angle of the table 30 while change in shape of the table 30 is being ignored.

FIG. 4 shows the respective positions of the table 30 when the table 30 is slid by the distance z0, z1, or z2 from the reference position 0. At the position 300, vertical displacement of the table 30 and change in angle from the horizontal direction are relatively small. Further, adjustment is performed at the position 300 such that the table 30 is not deflected.

When the table 30 is slid by the distance z1 (z1>z0) from the reference 0, the table 30 is positioned at the position 301 where the table 30 and the object P are slightly tilted to the lower right on the sheet of FIG. 4. Further, when the table 30 is slid by a distance z2 (z2>z1) from the reference 0, the table 30 is positioned at the position 302 where the table 30 and the object P are so inclined that displacement (step) occurs in the head of the object P against the foot of the object P.

For this reason, the X-ray CT apparatus 1 according to the present embodiment calculates displacement of the table 30 in the vertical direction and the angle of the table 30 from the horizontal direction by using data acquired by a prescan. On the basis of the calculated displacement and angle of the table 30, the vertical position of the table 30 and the tilt angle of the gantry 11a in the horizontal direction are set by the X-ray CT apparatus 1 so as to be kept constant at the time of the main scan.

Next, an operation of the X-ray CT apparatus 1 according to the present embodiment will be described with reference to the flowchart shown in FIG. 5.

(Table-Position Correction Processing)

Figure 5:
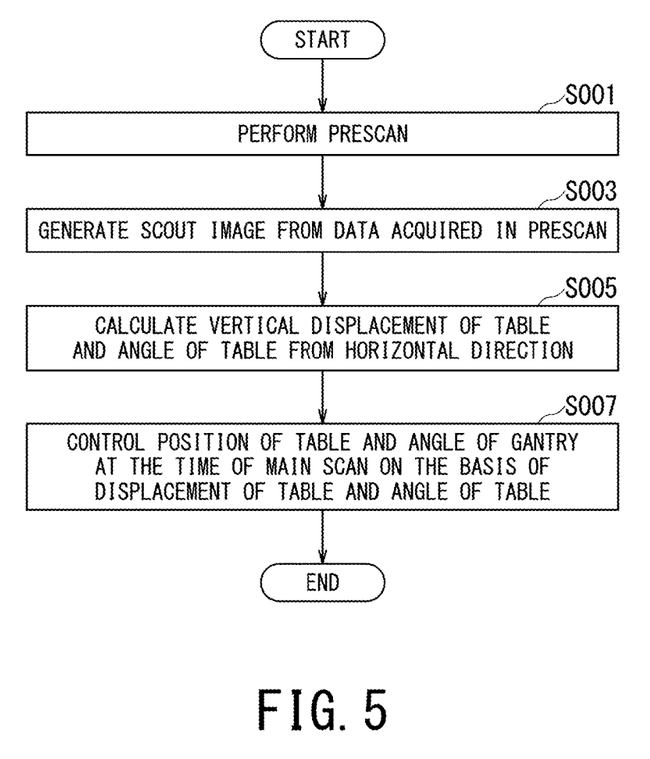
FIG. 5 is a flowchart illustrating the operation of the X-ray CT apparatus according to the present embodiment.

FIG. 5 is a flowchart illustrating the operation of the X-ray CT apparatus 1 according to the present embodiment.

First, in the step S001, the X-ray CT apparatus 1 images the object P by performing a prescan on the object P. The X-ray CT apparatus 1 controls the controller 32 of the scanner 11 so as to acquire raw data for generating a scout image. For instance, the scan control function 51 of the X-ray CT apparatus 1 controls the controller 32 such that tube current and tube voltage are supplied from the X-ray high-voltage circuit 26 to the X-ray tube 21 and the object P is irradiated with X-rays.

For instance, the scan control function 51 performs the prescan such that slice width of the raw data has the predetermined slice width by using which the angle of the table 30 can be calculated. For instance, the scan control function 51 performs simultaneous multi-slice imaging in which slice data within the predetermined slice width are simultaneously acquired by one imaging. In the prescan, data are acquired by repeating the simultaneous multi-slice imaging while the table 30 is being moved.

Figure 6A:
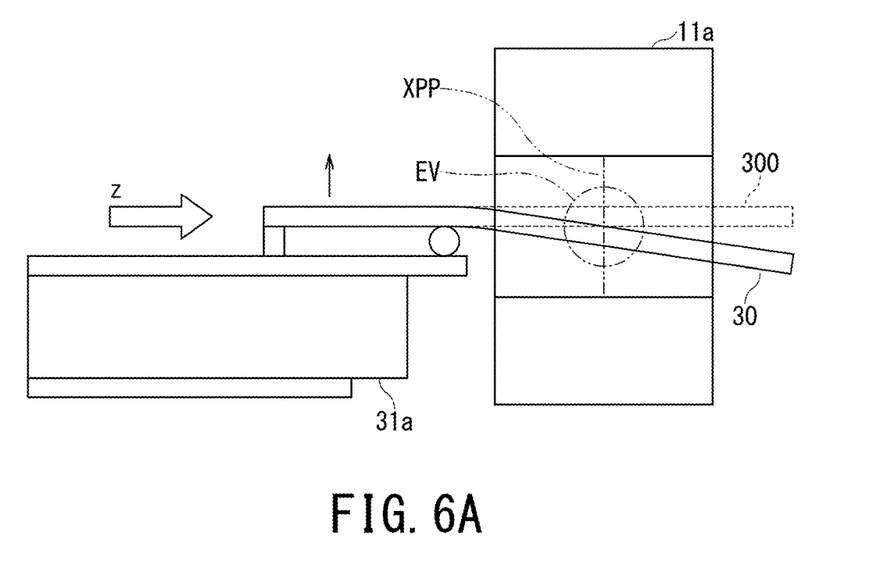
FIG. 6A and FIG. 6B are diagrams illustrating the displacement dh of the table in the vertical direction and the angle dθ of the table from the horizontal direction, both of which are calculated from the data acquired in the prescan performed by the X-ray CT apparatus according to the present embodiment.
Figure 6B:
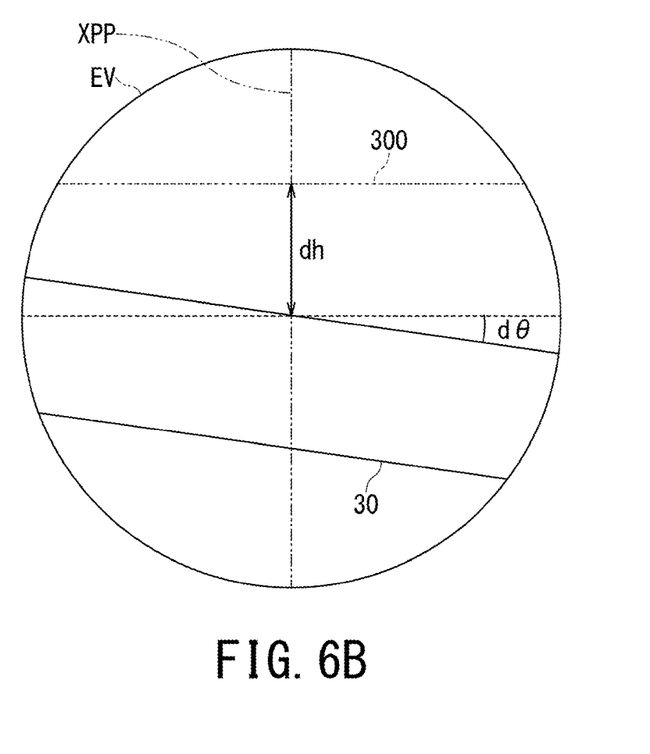

FIG. 6A and FIG. 6B are diagrams illustrating the displacement dh of the table 30 in the vertical direction and the angle dθ of the table 30 from the horizontal direction, both of which are calculated from the data acquired in the prescan performed by the X-ray CT apparatus 1 according to the present embodiment.

As Shown in FIG. 6A and FIG. 6B, positions through which X-rays pass between the X-ray tube 21 and the X-ray detector 23 in the gantry 11a are defined as X-ray pass positions XPP, the vertical displacement dh of the table 30 and the inclination angle dθ of the table 30 at the X-ray pass positions XPP are calculated from the data acquired by the prescan. Further, each of the vertical displacement dh and the inclination angle dθ of the table 30 is calculated depending on the position z of the table 30. The region EV is a region through which the table 30 passes at the X-ray pass positions XPP, and FIG. 6B is an enlarged view of the region EV in FIG. 6A.

In the next step S003, the X-ray CT apparatus 1 generates a scout image by performing the prescan. The X-ray CT apparatus 1 performs correction processing such as logarithmic conversion and sensitivity correction on the detection data inputted from the DAS 24 of the scanner 11 so as to generate projection data, and stores the generated projection data in the HDD 43. For instance, the scout-image generation function 52 of the X-ray CT apparatus 1 generates projection data of plural cross-sections orthogonal to the Z direction on the basis of the projection data inputted from the HDD 43, and generates a scout image on the basis of the projection data of the plural cross-sections, and stores the scout image in the HDD 43. The scout image is generated from slice data within the predetermined slice width on which simultaneous multi-slice imaging is repeatedly performed.

Figure 7:
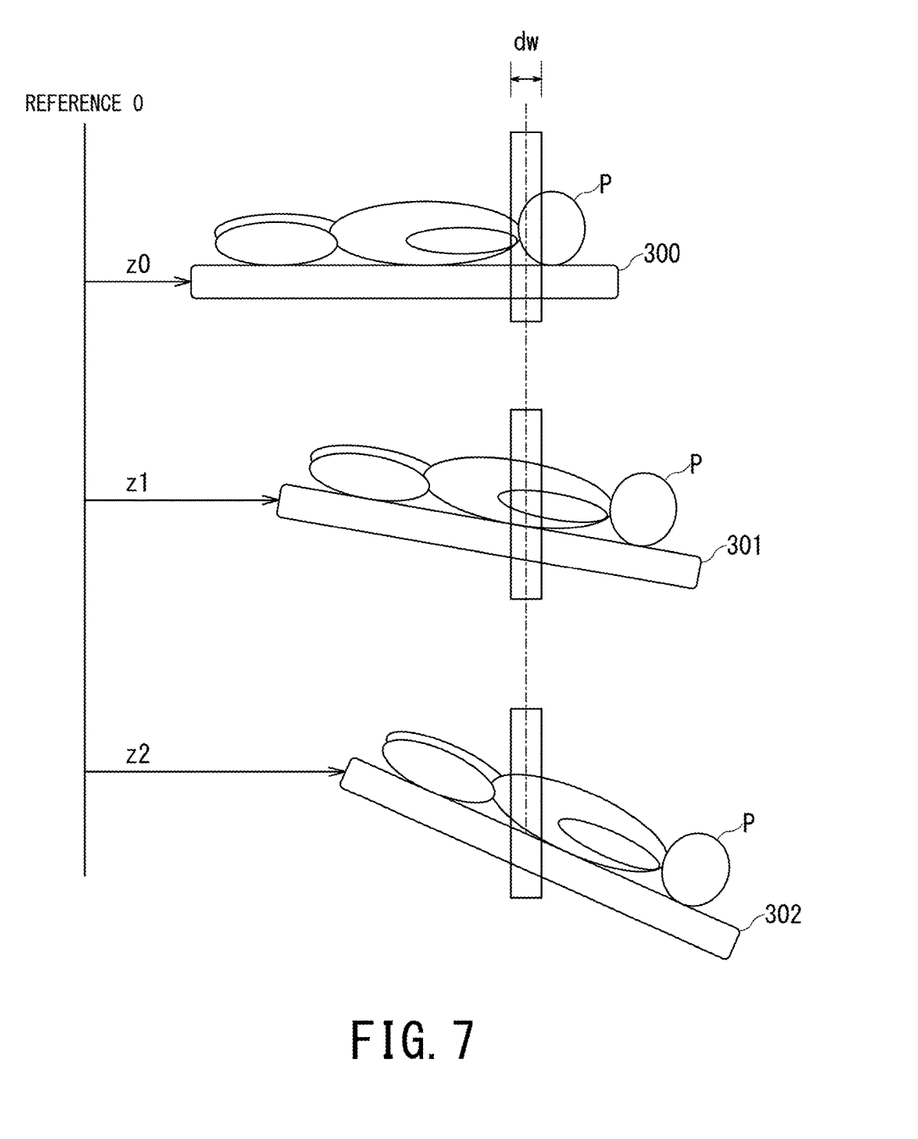
FIG. 7 is a schematic diagram illustrating a concept that multi-slice data are continuously generated for the object P by the scout-image generation function according to the present embodiment.

FIG. 7 is a schematic diagram illustrating a concept that multi-slice data are continuously generated for the object P by the scout-image generation function 52 according to the present embodiment.

As shown in FIG. 7, while the bed 31a is moving the table 30 from the position 300 to the position 302, the scan control function 51 continuously images each instant of movement of the table 30 in conjunction with the movement of the table 30.

In the case of FIG. 7, slice width of the multi-slice is assumed to be dw, and the scout-image generation function 52 continuously generates slice data at the instant of each movement of distance z0, distance z1, and distance z2.

In the next step S005, the X-ray CT apparatus 1 calculates the displacement of the table 30 in the vertical direction and the angle of the table 30 from the horizontal direction by using the data acquired by the prescan. The calculation function 53 of the X-ray CT apparatus 1 calculates the displacement dh of the table 30 with respect to the distance z from the reference 0 and the inclination angle dθ of the table 30 with respect to the distance z from the reference 0 by using, e.g., the slice data imaged as the prescan.

As an example here, the present embodiment is given of a case where the table 30 does not deflect at the position 300 of the distance z0, and therefore the displacement dh of the table 30 with respect to that of the distance z0 and the inclination angle dθ of the table 30 with respect to that of the distance z0 are calculated.

Figure 8:
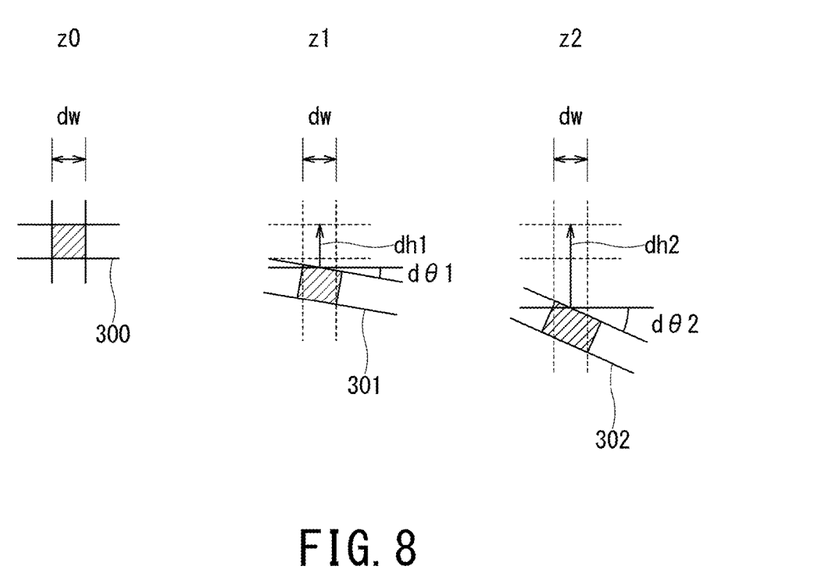
FIG. 8 is a schematic diagram illustrating the concept of calculating the displacement dh of the table and the inclination angle dθ of the table at each distance z to be performed by the calculation function of the X-ray CT apparatus according to the present embodiment.

FIG. 8 is a schematic diagram illustrating the concept of calculating the displacement dh of the table 30 and the inclination angle dθ of the table 30 at each distance z to be performed by the calculation function 53 of the X-ray CT apparatus 1 according to the present embodiment.

FIG. 8 shows the state in which the displacement dh and inclination angle dθ of the table 30 at each distance z in FIG. 7 are viewed from the same direction as in FIG. 7. When the sliding distance of the table 30 is the distance z0, the table 30 is at the position 300 and both of the displacement dh and inclination angle dθ of the table 30 are adjusted to be zero.

When the sliding distance of the table 30 is the distance z1, the table 30 is at the position 301, the displacement dh of the table 30 is displacement dh1, and the inclination angle dθ of the table 30 is dθ1. Further, when the sliding distance of the table 30 is the distance z2, the table 30 is at the position 302, the displacement dh of the table 30 is increased to displacement dh2, and the inclination angle dθ of the table 30 is increased to dθ2.

Figure 9A:
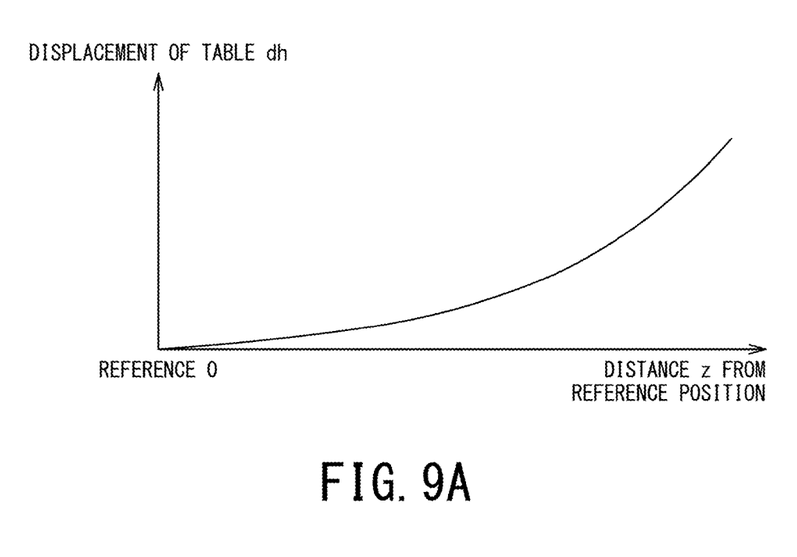
FIG. 9A and FIG. 9B are graphs obtained by continuously plotting the displacement dh and the inclination angle dθ of the table, which are calculated by the calculation function of the X-ray CT apparatus according to the present embodiment.
Figure 9B:
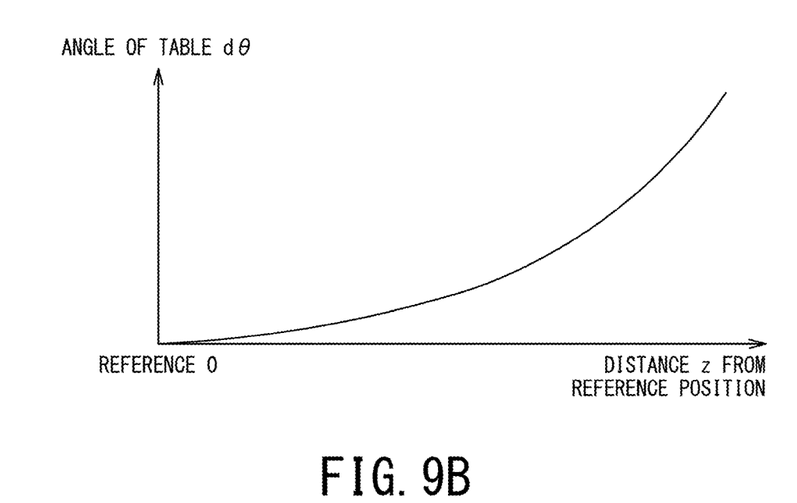

FIG. 9A and FIG. 9B are graphs obtained by continuously plotting the displacement dh and the inclination angle dθ of the table 30, which are calculated by the calculation function 53 of the X-ray CT apparatus 1 according to the present embodiment.

FIG. 9A shows a graph obtained by continuously plotting the displacement dh of the table 30 with respect to the distance z from the reference 0 calculated by the calculation function 53 of the X-ray CT apparatus 1. FIG. 9B shows a graph obtained by continuously plotting the inclination angle dθ of the table 30 with respect to the distance z from the reference 0 calculated by the calculation function 53 of the X-ray CT apparatus 1.

FIG. 9A and FIG. 9B indicate that the displacement dh of the table 30 and the inclination angle dθ of the table 30 increase as the distance z from the reference 0 increases.

In the next step S007, the X-ray CT apparatus 1 controls the position of the table 30 and the angle of the gantry 11a at the time of the main scan on the basis of the displacement of the table 30 and the angle of the table 30. At the time of execution of the main scan, for instance, the drive control function 54 of the X-ray CT apparatus 1 controls the table driving circuit 31 and the tilt driving circuit 28 via the controller 32 on the basis of the displacement dh of the table 30 with respect to the distance z from the reference 0 and the inclination angle dθ of the table 30 with respect to the distance z from the reference 0 so as to correct the position of the table 30 and the angle of the gantry 11a.

The drive control function 54 of the X-ray CT apparatus 1 controls the table driving circuit 31 and the tilt driving circuit 28 by using, e.g., a graph showing the displacement dh of the table 30 and a graph showing the inclination angle dθ of the table 30 such that the table 30 is constantly kept at the position 300. In this case, the drive control function 54 continuously controls the displacement of the table 30 and the inclination of the gantry 11a so as to cancel the displacement dh of the table 30 and the inclination angle dθ of the table 30.

Figure 10:
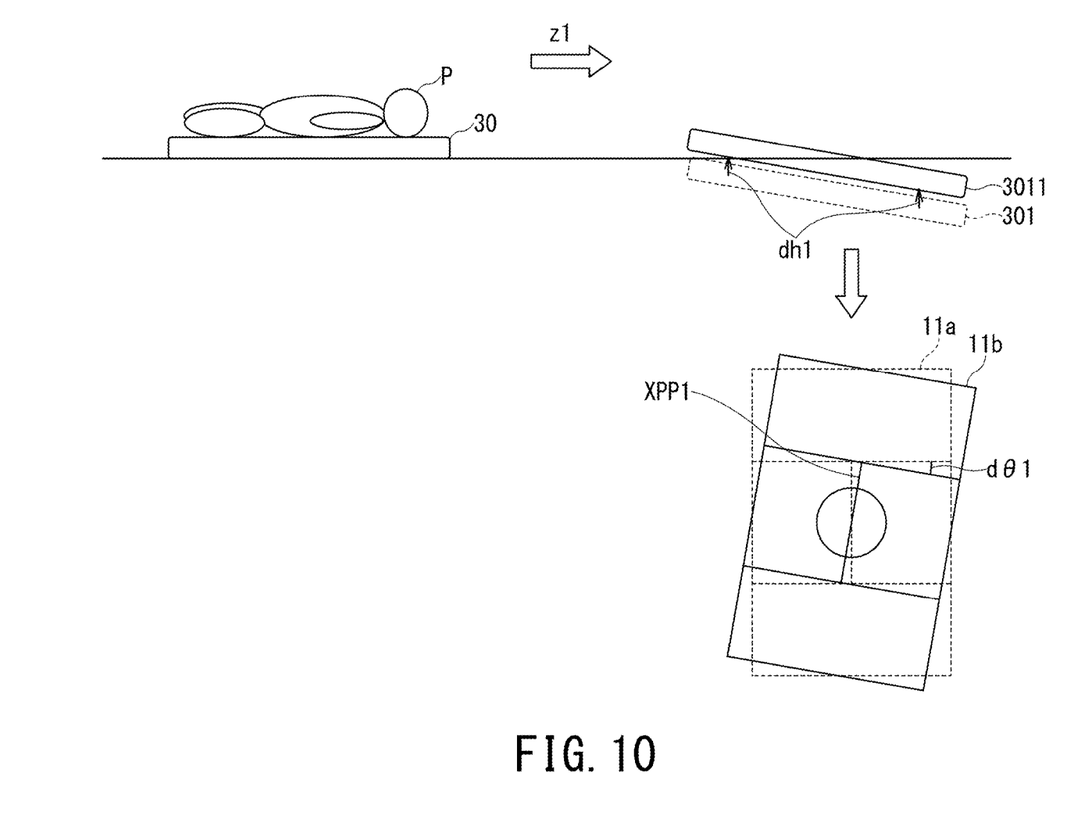
FIG. 10 is a schematic diagram illustrating a concept that the drive control function of the X-ray CT apparatus according to the present embodiment controls the table driving circuit and the tilt driving circuit so as to correct the position of the table and the angle of the gantry when the sliding distance is the distance z1 in FIG. 7.

FIG. 10 is a schematic diagram illustrating a concept that the drive control function 54 of the X-ray CT apparatus according to the present embodiment controls the table driving circuit 31 and the tilt driving circuit 28 so as to correct the position of the table 30 and the angle of the gantry 11a when the sliding distance is the distance z1 in FIG. 7.

As shown in FIG. 10, assuming that the bed 31a slides the table 30 by the distance z1 under the state where the object P is placed on the table 30, the table 30 moves to the position 301. In this case, the table driving circuit 31 corrects the displacement dh1 of the table 30, and the height of the table 30 is adjusted to the position 3011. Further, the angle of the gantry 11a is adjusted by the tilt driving circuit 28 so as to become the inclination dθ1 of the gantry 11b virtually illustrated in FIG. 10. As a result, the X-ray pass positions XPP1 become perpendicular to the horizontal direction of the table 30 at the position 3011.

As described above, the volume data acquired by the main scan at the position 3011 are acquired, e.g., in the state of the table 30 having the same height of the table 30 at the position 300 in FIG. 7 and the X-ray pass being perpendicular to the horizontal direction at the position 301. Thus, for instance, it is possible to avoid occurrence of a step in an acquired image when a cross-section of the table 30 becomes oblique at the time of a helical scan and/or when imaging is performed by a step-and-shoot scan. As a result, an image with higher accuracy can be obtained than conventional technology, and thus misdiagnosis can be prevented.

Figure 11:
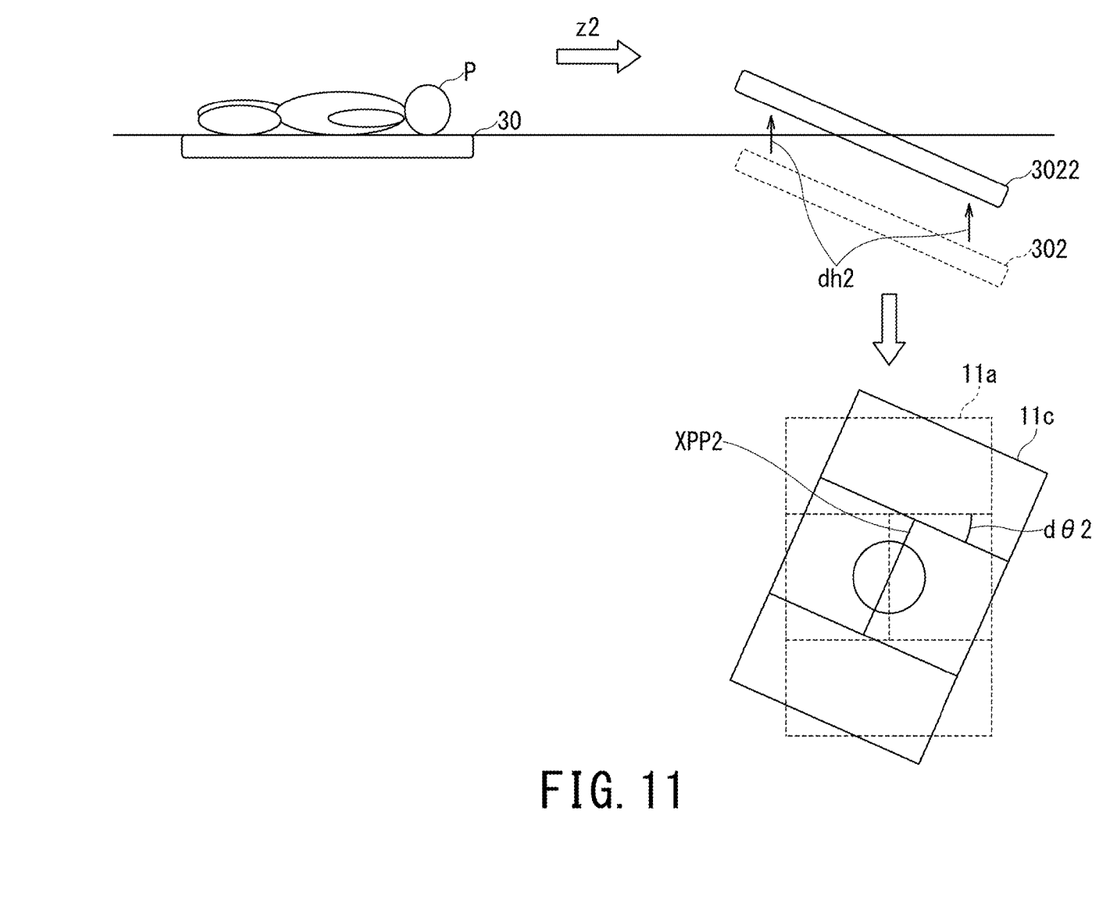
FIG. 11 is a schematic diagram illustrating a concept that the drive control function of the X-ray CT apparatus according to the present embodiment controls the table driving circuit and the tilt driving circuit so as to correct the position of the table and the angle of the gantry when the sliding distance is the distance z2 in FIG. 7.

FIG. 11 is a schematic diagram illustrating a concept that the drive control function 54 of the X-ray CT apparatus according to the present embodiment controls the table driving circuit 31 and the tilt driving circuit 28 so as to correct the position of the table 30 and the angle of the gantry 11a when the sliding distance is the distance z2 in FIG. 7.

As shown FIG. 11, assuming that the bed 31a slides the table 30 by the distance z2 under the state where the object P is placed on the table 30, the table 30 moves to the position 302. In this case, the table driving circuit 31 corrects the displacement dh2 of the table 30 and adjusts the height of the table 30 to the position 3022. Further, the tilt driving circuit 28 adjusts the tilt angle of the gantry 11a such that the tilt angle of the gantry 11a becomes the tilt angle dθ2 of the gantry 11c virtually illustrated in FIG. 11. In this manner, the X-ray path positions XPP2 become perpendicular to the horizontal direction of the table 30 at the position 3022.

As described above, the volume data acquired by the main scan at the position 3022 are imaged, e.g., in the state of having the table 30 the same height of the table 30 at the position 300 in FIG. 7 and the X-ray pass being perpendicular to the horizontal direction of the position 302. Accordingly, it is possible to avoid occurrence of a step in the acquired image when a cross-section of the table 30 becomes oblique at the time of a helical scan and/or when imaging is performed by a step-and-shoot scan. As a result, an image with higher accuracy can be obtained than conventional technology, and thus misdiagnosis can be prevented.

As described above, the X-ray CT apparatus 1 according to the present embodiment includes the gantry 11 equipped with the X-ray tube 21 and the X-ray detector 23, the table 30 for placing the object P, the bed 31a equipped with the table driving circuit 31 for inserting the table 30 into the opening of the gantry 11a, and the processing circuitry 41.

The processing circuitry 41 of the X-ray CT apparatus 1 includes the scan control function 51 for performing a main scan and a prescan to be performed prior to the main scan, the calculation function 53 for calculating the vertical displacement of the table 30 and the angle of the table 30 from the horizontal direction by using data acquired by the prescan, and the drive control function 54 for controlling the position of the table 30 and the angle of the gantry 11a at time of the main scan on the basis of the displacement of the table 30 and the angle of the table 30.

Thus, for instance, the X-ray CT apparatus 1 according to the present embodiment can correct the displacement of the table 30 and the inclination of the table 30 such that the table 30 crosses X-ray pass positions XPP always at the same position with respect to the predetermined position of the gantry 11a. Thus, it is possible to acquire a high-definition image and avoid misdiagnosis.

In addition, the drive control function 54 of the X-ray CT apparatus 1 can control the height of the table 30 in the bed 31a and the tilt angle of the gantry 11a such that the table 30 crosses the center of the X-ray pass positions XPP formed by the X-ray tube 21 and the X-ray detector 23.

Although a description has been given of the case where displacement and inclination is generated in the table 30 due to weight of the object P in the present embodiment as shown in FIG. 7, the present embodiment is not limited to such a case. It is previously assumed that predetermined weight is applied to the table 30, and the table 30 is deflected depending on sliding distance of the table 30. However, in the case of a light-weight object P, the table 30 is not deflected to a predetermined amount even when the table 30 moves, rather it is expected to warp. Even in such a case, the calculation function 53 can calculate the angle of the table 30 by a prescan with the predetermined slice width and can correct the position of the table 30 such that the table 30 always crosses the same position.

Although the displacement of the table 30 and the inclination angle of the table 30 are corrected in terms of hardware in the present embodiment, the present embodiment is not limited to such an aspect. For instance, the inclination of the table 30 may be corrected in terms of software by using data from which the inclination of the table 30 can be calculated, e.g., data with the predetermined slice width.

Further, although a description has been given of the case where the object P is continuously imaged when the scan control function 51 performs a prescan in the present embodiment, the present embodiment is not limited to such an aspect. For instance, in a prescan, the object P may be imaged by a step and shoot scan. In this case, X-ray irradiation is stopped after irradiating a portion of the object P with X-rays, then the table 30 is slid by predetermined sliding distance, and then the object P can be imaged by pulse X-rays at a predetermined position.

According to at least one of the above-described embodiments, the X-ray CT apparatus 1 can acquire a high-definition image by correcting the displacement and inclination of the table 30 with hardware, and thus it is possible to avoid misdiagnosis.

The X-ray tube 21 in the above-described embodiments is one aspect of the X-ray source recited in the claims. The processing circuitry 41 in the above-described embodiments is one aspect of the processing circuitry recited in the claims.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

The invention claimed is:

1. An X-ray CT apparatus comprising:
   a gantry equipped with an X-ray source and an X-ray detector;
   a table on which an object is placed;
   a bed including a moving mechanism which is configured to move the table in a horizontal direction and in a vertical direction; and
   processing circuitry configured to
   perform a main scan and a prescan, the prescan being performed prior to the main scan,
   calculate displacement of the table in the vertical direction and an angle of the table from the horizontal direction using data acquired in the prescan, and
   control a position of the table and an angle of the gantry based on the displacement of the table and the angle of the table.

2. The X-ray CT apparatus according to claim 1,
   wherein the processing circuitry is configured to perform the prescan in such a manner that slice width of the data acquired in the prescan has a predetermined slice width from which the angle of the table is calculable.

3. The X-ray CT apparatus according to claim 1,
   wherein the processing circuitry is configured to perform the prescan in such a manner that the object is consecutively imaged during the prescan.

4. The X-ray CT apparatus according to claim 1, further comprising a tilt driving circuit configured to tilt the gantry in a longitudinal direction of the table,
   wherein the processing circuitry is configured to
   control the moving mechanism of the bed based on information on the displacement of the table to adjust height of the table, and
   control the tilt driving circuit based on information on the angle of the table to adjust a tilt angle of the gantry is adjusted.

5. The X-ray CT apparatus according to claim 1,
   wherein the processing circuitry is configured to control a tilt angle of the gantry according to a position of the table in the horizontal direction in such a manner that a direction from the X-ray source to the X-ray detector is orthogonal to a longitudinal direction of the table at each imaging position of the object.

6. The X-ray CT apparatus according to claim 1,
   wherein the processing circuitry is configured to control height of the table according to a position of the table in the horizontal direction in such a manner that the height of the table is kept constant at each imaging position of the object.

* * * * *